(12) United States Patent
Purcell et al.

(10) Patent No.: US 8,391,565 B2
(45) Date of Patent: Mar. 5, 2013

(54) SYSTEM AND METHOD OF DETERMINING NITROGEN LEVELS FROM A DIGITAL IMAGE

(75) Inventors: Larry C Purcell, Fayetteville, AR (US); Robert L. Rorie, Fayetteville, AR (US); Douglas E Karcher, Fayetteville, AR (US)

(73) Assignee: Board of Trustees of the University of Arkansas, Little Rock, AK (US)

( * ) Notice: Subject to any disclaimer, the term of this patent is extended or adjusted under 35 U.S.C. 154(b) by 325 days.

(21) Appl. No.: 12/800,849

(22) Filed: May 24, 2010

(65) Prior Publication Data

US 2011/0286636 A1 Nov. 24, 2011

(51) Int. Cl.
G06K 9/00 (2006.01)
(52) U.S. Cl. ........................................ 382/110
(58) Field of Classification Search ................... 382/110
See application file for complete search history.

(56) References Cited

U.S. PATENT DOCUMENTS

| | | | |
|---|---|---|---|
| 5,606,821 A | 3/1997 | Sadjadi et al. | |
| 6,160,902 A | 12/2000 | Dickson et al. | |
| 6,466,321 B1 | 10/2002 | Satake et al. | |
| 6,529,615 B2 | 3/2003 | Hendrickson et al. | |
| 6,567,537 B1 | 5/2003 | Anderson | |
| 6,683,970 B1 | 1/2004 | Satake et al. | |
| 6,734,973 B1 | 5/2004 | Mutters et al. | |
| 6,792,882 B2 * | 9/2004 | Aspelin et al. | 111/118 |
| 6,813,544 B2 | 11/2004 | Hood et al. | |
| 7,103,451 B2 | 9/2006 | Seal et al. | |
| 7,184,859 B2 | 2/2007 | Hood et al. | |
| 7,362,439 B2 | 4/2008 | Franzen et al. | |
| 7,408,145 B2 | 8/2008 | Holland | |
| 7,547,508 B1 * | 6/2009 | Lefcourt et al. | 435/4 |
| 7,570,783 B2 * | 8/2009 | Wei et al. | 382/100 |
| 7,723,660 B2 | 5/2010 | Holland | |
| 7,929,141 B2 | 4/2011 | Franzen et al. | |
| 8,208,680 B2 * | 6/2012 | Scharf et al. | 382/100 |
| 2001/0016053 A1 | 8/2001 | Dickson et al. | |
| 2001/0036295 A1 | 11/2001 | Hendrickson et al. | |
| 2004/0032973 A1 | 2/2004 | Robeson et al. | |
| 2006/0039603 A1 | 2/2006 | Koutsky | |
| 2008/0304711 A1 | 12/2008 | Scharf et al. | |
| 2011/0047867 A1 | 3/2011 | Holland | |

OTHER PUBLICATIONS

Peter C. Scharf et al. Calibrating Reflectance Measurements to Predict Optimal Sidedress Nitrogen Rate for Corn, Agronomy Journal, 2009, vol. 101, Issue 3, Columbia, Missouri.
Peter C. Scharf et al. Chlorophyll Meter Readings Can Predict Nitrogen Need and Yield Response of Corn in the North-Central USA, Reproduced from Agronomy Journal, 2006, Columbia, Missouri.

(Continued)

Primary Examiner — Tom Y Lu
(74) Attorney, Agent, or Firm — Head, Johnson & Kachigian, P.C.

(57) ABSTRACT

A system and method of determining nitrogen levels from a digital image. In particular, a method of determining leaf nitrogen concentration and yield from a digital photograph of a fully developed leaf (collared leaf) of a crop of nonlegumes, such as corn, rice, wheat, cotton, potatoes or sugarcane. The digital image is processed to determine a dark green color index ("DGCI"), which is closely related to leaf nitrogen concentration and yield. Standardized color disks having known DGCI values are included in the digital photograph and serve as an internal standard. The internal standard allows correction of DGCI of samples when using different cameras and/or when lighting conditions change.

27 Claims, 11 Drawing Sheets

OTHER PUBLICATIONS

Simone Graeff et al. Quantifying Nitrogen Status of Corn (*Zea mays* L.) in the Field by Reflectance Measurements, European Journal of Agronomy, 2003, Stuttgart, Germany.

Douglas E. Karcher et al. Quantifying Turfgrass Color Using Digital Image Analysis, Crop Science, 2003, Fayetteville, Arkansas.

Karcher, Douglas E., Quantifying Turfgrass Color Using Digital Image Analysis, Crop Science, vol. 43: 943-951; May-Jun. 2003. Dept. of Horiculture, Univ. of Arkansas; U.S.

Murakami, Paula F., An Instructional Guide for Leaf Color Analysis using Digital Imaging Software, Forest Service, Northeastern Research Station, General Technical Report NE-327; May 2005. USDA Forest Service Publications Distribution. U.S.

Yaju, Liu, et al., A Research in the Application of Computer-Vision to Plant Growth Monitoring Oct. 2007; pp. 522-526; School of Mechanical and Electrical Engineering, Hebei Agricultural University;Hebei, China.

Patton, Aaron, et. al., Using Digital Image Analysis to Quantify Turfgrass Cover and Disease. Nov. 2009; U.S.

Kyveryga, P.M., Using Late-Season Uncalibrated Digital Aerial Imagery for Predicting Corn Nitrogen Status within Fields; Jul. 2010; Laboratory for Applied Spatial Analysis, Southern Illinois University, Edwardsville, Illinois; U.S.

\* cited by examiner

SYSTEM AND METHOD OF DETERMINING NITROGEN LEVELS FROM A DIGITAL IMAGE

BACKGROUND OF THE INVENTION

1. Field of the Invention

This invention relates generally to a system and method of determining nitrogen levels from a digital image, and more particularly to a system and method of determining leaf nitrogen concentration and/or crop yield from a digital image of fully developed leaves (collared leaf) of a crop of nonlegumes, such as corn, rice, wheat, cotton, potatoes or sugarcane.

2. Description of the Related Art

Management of fertilizer nitrogen is a critical component for producing consistent crop yields. Nitrogen fertilizer also represents a considerable input cost and has serious environmental consequences if over applied. Therefore, it is important to apply the correct amount of fertilizer to meet the crop's need but not to supply more than is required because of the cost and environmental concerns.

There are few tools that are currently available to help farmers determine if crop nitrogen levels during the season are adequate, and several techniques have been used to objectively measure crop color, including reflectance measurements, chlorophyll and amino acid analysis, and comparison with standardized colors. All of these techniques have certain disadvantages compared with subjective color ratings. Reflectance, chlorophyll, and amino acid measurements all require relatively expensive equipment, and transport of samples to a laboratory for analysis. In addition, correlations between color and chlorophyll or amino acid measurements are either species or cultivar dependent. A hand-held SPAD meter (Minolta) gives real-time chlorophyll concentration of leaves in the field, and chlorophyll concentration has a close relationship to leaf nitrogen concentration. In the Midwest, SPAD meter measurements are closely associated with leaf nitrogen and have a positive relationship with yield. (Schepers, et al., "Comparison of corn leaf nitrogen concentration and CM readings." *Commun. Soil Sci. Plant Anal.* 1992, 23:2173-87; Scharf, et al., "Chlorophyll meter readings can predict nitrogen needs and yield in response of corn in North-Central USA." *Agron. J.* 2006, 98:655-65). Disadvantages of the SPAD meter include a large initial equipment cost and that a large number of measurements may be required to make a representative measurement.

In recent years, digital photography has become a common and affordable means for the scientific community to document and present images. Digital cameras, in conjunction with image analysis software, are being used to quantify wheat (*Triticum aestivum* L.) senescence (Adamsen, et al., "Measuring wheat senescence with a digital camera." *Crop Sci.* 1999, 39:719-724) and canopy coverage in wheat (Lukina, et al., "Estimating vegetation coverage in wheat using digital images." *J. Plant Nutr.* 1999, 22:341-350) and soybeans [*Glycine max* L. (Merr.)] (Purcell, L. C., "Soybean canopy coverage and light interception measurements using digital imagery." *Crop Sci.* 2000, 40:834-837). Through digital photography, researchers can instantaneously obtain millions of bits of information on a relatively large crop canopy. For example, a digital image taken of a crop using a 1280×960 pixel resolution contains 1,228,800 pixels, with each pixel containing independent color information about the crop.

The information contained in each digital image includes the amount of red, green and blue ("RGB") light emitted for each pixel in the digital image. Although it may be intuitive to use the green levels of the RGB information to quantify the green color of the digital image, the intensity of red and blue will confound how green the digital image appears. To ease the interpretation of digital color data, RGB values can be converted directly to hue, saturation and brightness ("HSB") values that are based on human perception of color. In HSB color description, hue is defined as an angle on a continuous circular scale from 0° to 360° (0°=red, 60°=yellow, 120°=green, 180°=cyan, 240°=blue, 300°=magenta), saturation is the purity of the color from 0% (gray) to 100% (fully saturated color), and brightness is the relative lightness or darkness of the color from 0% (black) to 100% (white).

It is therefore desirable to provide a system and method of determining nitrogen levels from a digital image that does not require specialized, expensive equipment.

It is further desirable to provide a system and method of determining nitrogen levels from a digital image where the digital image can easily be sent electronically, such as via email or to a web-based server, for immediate analysis.

It is still further desirable to provide a system and method of determining nitrogen levels from a digital image that integrates values over a much larger leaf sample than does the SPAD meter.

It is yet further desirable to provide a system and method of determining nitrogen levels from a digital image, which does not rely on chemical processes of measuring leaf nitrogen.

It is yet further desirable to provide a system and method of determining nitrogen levels from a digital image having a quick turn-around time to provide farmers with real-time nitrogen concentration and yield information for the crop.

SUMMARY OF THE INVENTION

In general, in a first aspect, the invention relates to a method for determining nitrogen levels of a nonlegume plant by acquiring an image with digital photography of a colored leaf from a crop of nonlegume plants against a background, performing an algorithm to determine a corrected dark green color index of the leaf in the image, and determining leaf nitrogen sufficiency or deficiency of the leaf in the image from the corrected dark green color index. The image includes an internal standard to account for differences in cameras and/or lighting conditions of the digital photography. The background has a color in a portion of the visible spectrum away from the visible spectrum of the color of the leaf.

The internal standard may include standardized color disks having a predetermined shape and a color representing a color value ranging from severely nitrogen deficient to nitrogen sufficient of the leaf, such as a first standardized color disk having a yellow color representing a severely nitrogen deficient leaf and a second standardized disk having a dark green color representing a nitrogen sufficient leaf against a pink background. The method may include placing the standardized color disks a distance away from the leaf during the digital photography to minimize any shadows between the leaf and the standardized color disks. In addition, the algorithm recognizes the shape of the standardized color disks and uses the standardized color disks as the internal standard to adjust for different cameras and/or lighting conditions.

The algorithm of the method for determining nitrogen levels of the nonlegume plant can further include the steps of calculating a dark green color index of the leaf in the digital image, calculating a dark green color index of the standardized color disks in the image, and calculating a corrected leaf dark green color index from the dark green color index of the leaf and the dark green color index of the standardized color disks. The step of calculating the dark green color index of the leaf in the image may include obtaining absolute red, green and blue values of the leaf in the image, converting the absolute red, green and blue values to percentage red, green and blue values of the leaf in the image, converting the percentage red, green and blue values to absolute hue, saturation and brightness values of the leaf in the image, calculating average hue, saturation and brightness values from the absolute hue, saturation and brightness values of the leaf in the image, and converting the average hue, saturation and brightness values to the dark green color index of the leaf in the image. Similarly, the step of calculating a dark green color index of the standardized color disks may include obtaining absolute red, green and blue values of the standardized color disks in the image, converting the absolute red, green and blue values to percentage red, green and blue values of the standardized color disks in the image, converting the percentage red, green and blue values to absolute hue, saturation and brightness values of the standardized color disks in the image, calculating average hue, saturation and brightness values from the absolute hue, saturation and brightness values of the standardized color disks in the image, and converting the average hue, saturation and brightness values to the dark green color index of the standardized color disks in the image. The dark green color index of the leaf and/or the standardized color disks in the image encompasses a dark green color on a scale of zero (0) to one (1) with values closer to one (1) representing a darker green.

Moreover, the method may also include the steps of estimating yield of the crop from the image as a function of the corrected dark green color index and further transmitting the yield of the crop. Additionally, the method may include estimating yield of the crop from the image based on the leaf nitrogen sufficiency or deficiency and/or transmitting the leaf nitrogen sufficiency or deficiency.

In general, in a second aspect, the invention relates to a system for determining nitrogen levels of a nonlegume plant comprising at least at least one electronic device for taking an image of a colored leaf from a crop of the nonlegume plant, an image background having a color in a portion of the visible spectrum away from the visible spectrum of the color of the leaf, and an internal standard to account for differences in cameras and/or lighting conditions of the image. The system may also include a central processing unit communicably attached to the electronic device via a network connection for performing an algorithm to determine a corrected dark green color index of the leaf in the image. Further, the electronic device may be a digital camera or a handheld device having a camera and an algorithm to determine a corrected dark green color index of said leaf in said image.

In addition, the internal standard may be standardized color disks having a predetermined shape and a color representing a color value ranging from severely nitrogen deficient to nitrogen sufficient of the leaf, such as a first standardized color disk having a yellow color representing a severely nitrogen deficient leaf and a second standardized disk having a dark green color representing a nitrogen sufficient leaf.

Furthermore, the nonlegume plant may be corn, rice, wheat, cotton, potatoes or sugarcane.

Other advantages and features will be apparent from the following description and from the claims.

DETAILED DESCRIPTION OF THE INVENTION

The systems and methods discussed herein are merely illustrative of specific manners in which to make and use this invention and are not to be interpreted as limiting in scope.

While the systems and methods have been described with a certain degree of particularity, it is to be noted that many modifications may be made in the details of the construction and the arrangement of the devices, components and/or steps without departing from the spirit and scope of this disclosure. It is understood that the systems and methods are not limited to the embodiments set forth herein for purposes of exemplification.

Figure 1A:
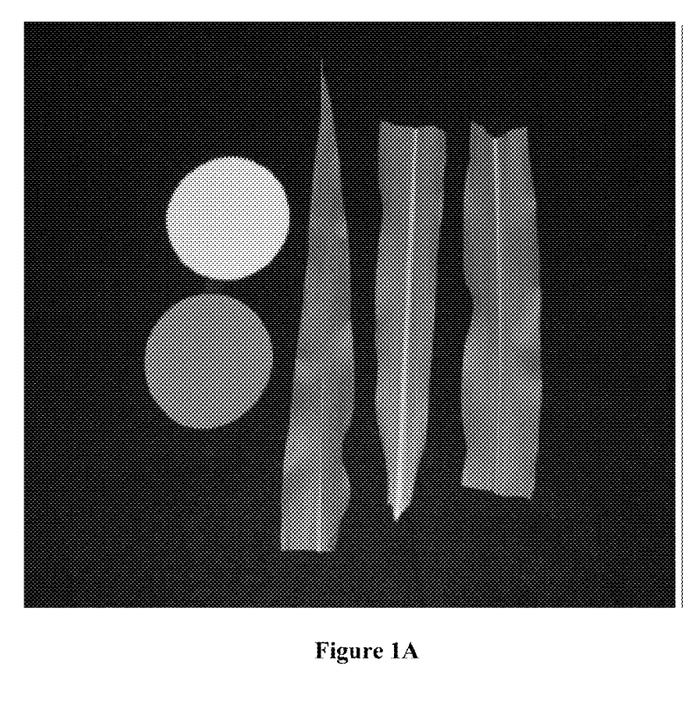
FIGS. 1A and 1B are digital images of uppermost collared corn leaves and standardized color disks against a black felt background (FIG. 1A) and a pink felt background (FIG. 1B) under normal fluorescent lighting in accordance with an illustrative embodiment of the system and method of determining nitrogen levels from a digital image disclosed herein.
Figure 1B:
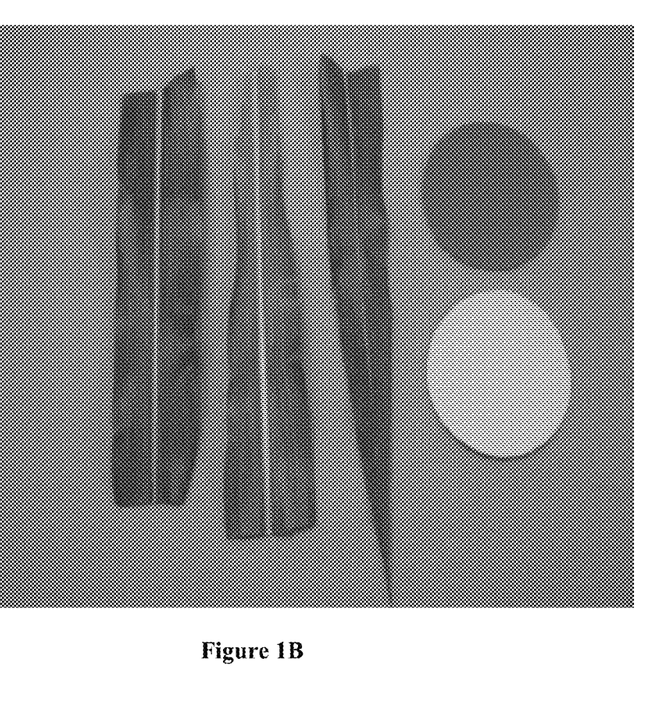
Figure 2A:
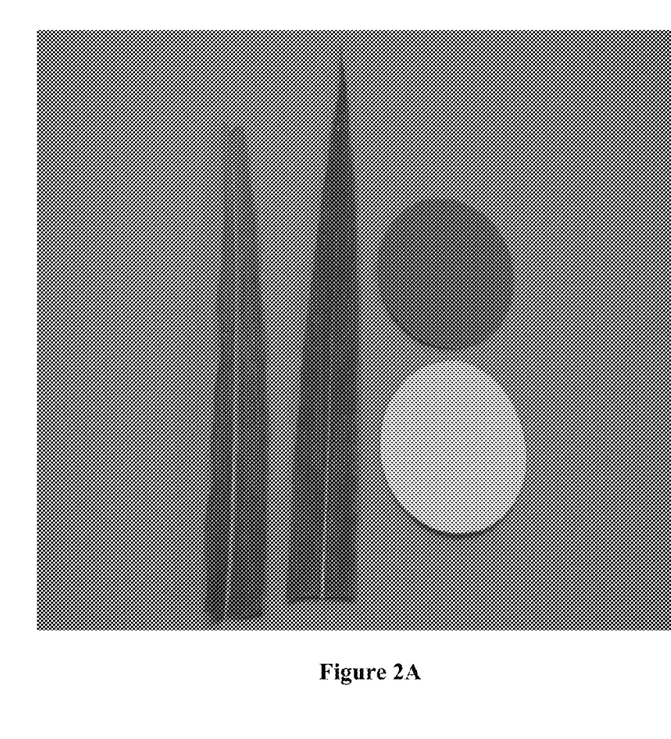
FIGS. 2A and 2B are digital images of uppermost collared corn leaves and standardized color disks before (FIG. 2A) and after (FIG. 2B) analysis using SigmaScan in accordance with an illustrative embodiment of the system and method of determining nitrogen levels from a digital image disclosed herein.
Figure 2B:
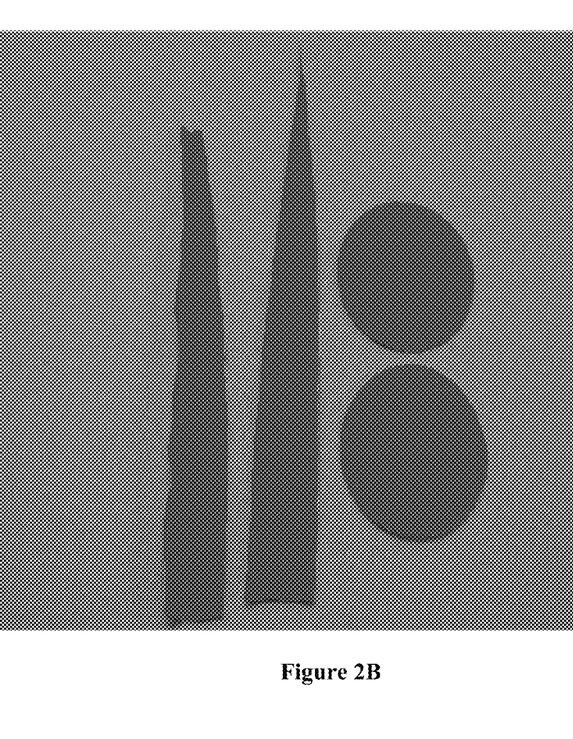

A system and method of determining nitrogen levels in nonlegume crops from a digital image is provided herein. As shown in FIGS. 1B and 2A, the leaf nitrogen sufficiency or deficiency and yield is determined from a digital image of a fully developed leaf of a nonlegume crop, such as corn, rice, wheat, cotton, potatoes or sugarcane, against a colored background. The colored background is in a portion of the visible spectrum furthest away from the green spectrum, in order to eliminate interference from reflection and other non-target sources. In addition to the leaf, an internal standard is included in each digital image to account for differences in cameras and/or lighting conditions. The internal standard may include a plurality of standardized color disks representing the range of green values typically found in the crop, ranging from severely nitrogen deficient to nitrogen sufficient. For example, the digital images of FIGS. 1B and 2A include uppermost, fully developed leaves and standardized color disks having green colors typically found in corn ranging from severely nitrogen deficient (yellow) to nitrogen sufficient (dark green) placed against a pink background. The standardized color disks should be placed a distance away from any leaf during photography to minimize any shadows between the leaf and the standardized color disks.

An algorithm of the system and method of determining nitrogen levels of leaf sections in a digital image recognizes the standardized color disks by their shape and uses them as the internal standard to adjust for different cameras and/or lighting conditions. The algorithm also converts the RGB spectra of the digital image to values of HSB, which are then converted to a DGCI value. The DGCI is a single value between zero (0) and one (1) and represents the "greenness" of the leaf samples and is closely related to the sufficiency or deficiency of nitrogen within the leaf and the yield. For each leaf segment in the digital image, the algorithm determines the DGCI and the area for that leaf segment. The algorithm calculates a single DGCI value for all of the leaf segments in the digital image from a weighted average of DGCI values of all leaf segments. The DGCI values of the standardized color disks are calibrated to the measured DGCI values using linear regression in order to eliminate any differences among the different cameras and/or lighting conditions. A two-point linear calibration for the known DGCI values of the internal standard is compared to the two-point linear calibration of the measured DGCI values of the internal standard, as determined by a particular camera. Correcting a camera's calibration to known values eliminates differences among cameras and/or lighting conditions. As can be seen from FIGS. 3 through 10, after correction, all combinations of DGCI values among the different cameras had correlation coefficients greater than 0.99 using the system and method of determining nitrogen levels of leaf sections in the digital image disclosed herein.

In general, the system and method of determining nitrogen levels of leaf sections in a digital image determines the average color of leaf sections by: (i) acquiring an image by digital photography, (ii) obtaining average RGB pixel values for the leaf sections within the digital image, and (iii) converting the RGB values to HSB values. The average RGB values of the digital images may be calculated using SigmaScan Pro 5.0 (SPSS, 1998). Using the predetermined threshold settings and the algorithm to average weighted RGB values, each digital image can be analyzed for individual objects within a predetermined threshold. The average red, average green, and average blue measurement settings are then used to obtain the average RGB levels for leaf sections in the digital image. Using the algorithm, the average RGB values can then be transferred into a spreadsheet (Microsoft Corporation, 1999) to facilitate the conversion of the RGB values to HSB values. The algorithm converts absolute RGB values (measured on a scale of 0 to 255) to percentage RGB values by dividing each value by 255. Percentage RGB values can then be converted to average HSB values using the algorithm as follows:

Hue:

If $\max(R,G,B)=R, 60\{(G-B)/[\max(R,G,B)-\min(R,G,B)]\}$

If $\max(R,G,B)=G, 60(2+\{(B-R)/[\max(R,G,B)-\min(R,G,B)]\})$

If $\max(R,G,B)=B, 60(4+\{(R-G)/[\max(R,G,B)-\min(R,G,B)]\})$

Saturation:

$[\max(R,G,B)-\min(R,G,B)]/\max(R,G,B)$

Brightness:

$\text{Max}(R,G,B)$.

The HSB values can then be further developed into the DGCI, which encompasses dark green color on a scale of zero (0) to one (1) with values closer to one (1) representing a darker green. The DGCI is created to measure the relative dark green color of the digital image using the following equation:

$$\text{DGCI value}=[(H-60)/60+(1-S)+(1-B)]/3. \qquad \text{Equation 1}$$

The DGCI is calculated from the average of transformed HSB values. Each transformed value measures dark green color on a scale of zero (0) to one (1). Since the hue of most crop images range between 60° (yellow) and 120° (green), the maximum dark green hue is assigned as 120°. Therefore, the dark green hue transform can be calculated as (hue−60)/60, so that hues of 60° and 120° yield dark green hue transforms of zero (0) and one (1), respectively. Since lower saturation and brightness values corresponded to darker green colors, (1—saturation) and (1—brightness) may be used to calculate the dark green saturation and brightness transforms, respectively. The average of the transformed HSB values yield a single measure of dark green color, the DGCI value, which ranges from zero (0) to one (1) with higher values corresponding to darker green color.

The algorithm also separately analyzes each object in the digital image and gives individual values, such as on a separate line in the spreadsheet. After all the objects are scanned, the algorithm can exclude values that have a shape factor near the standardized color disks and average all other values in order to provide a final leaf DGCI value. A separate DGCI value is calculated for each of the standardized color disks, along with a corrected DGCI value for each digital image taken with each camera. The difference between actual and known DGCI values from the cameras is linear. The first step in calibration is to determine the difference between observed DGCI values and the known DGCI values for the standardized color disks. The slope of this relationship is:

$$\text{Slope} = \frac{(\text{Known } DGCI \text{ of } 1^{st} \text{ Disk} - \text{Known } DGCI \text{ of } 2^{nd} \text{ Disk})}{(\text{Observed } DGCI \text{ of } 1^{st} \text{ Disk} - \text{Observed } DGCI \text{ of } 2^{nd} \text{ Disk})} \qquad \text{Equation 2}$$

Once the slope is determined, the Y intercept can be calculated as:

$$Y\ intercept = Known\ DGCI\ of\ 2^{nd}\ Disk - (Slope \times Observed\ DGCI\ for\ 2^{nd}\ Disk) \qquad \text{Equation 3}$$

The corrected DGCI, based on the internal standard, may then be calculated as follows:

$$Corrected\ leaf\ DGCI = (Slope \times Observed\ Leaf\ DGCI) + Y\ intercept \qquad \text{Equation 4}$$

Greenhouse Study 2008:

A greenhouse study was conducted to compare SPAD, leaf nitrogen sufficiency or deficiency and the DGCI in corn (*Zea mays* L.). Seeds of G90 sweet corn were sown on Jan. 8, 2008, in twenty-five (25) centimeter pots with an approximate soil volume of three (3) liters. The potting medium was a mixture of two-thirds LB2 potting mix having a vermiculite, perlite and peat mix (Sun Gro Co., Bellvue, Wash.) and one-third sifted Captina Silt Loam having a fine-silty, siliceous, active, mesic Typic Fragiudults (Arkansas Agriculture and Extension Center, Fayetteville, Ark.). Four (4) seeds were planted per pot and thinned to two (2) plants after emergence. Pots were supplied nitrogen from a modified Hoagland solution containing 0, 168, 336, 504, 672, or 840 milligrams nitrogen per two (2) liters in the form of nitrate ($NO_3^-$). Solution pH was adjusted to approximately 6.8 before being applied to a thirty (30) centimeter saucer underneath each of the pots. All pots were kept well-watered using deionized water. The study design was a randomized complete block with two (2) replications.

Plant sampling occurred at V3 to V5 stages and the uppermost collared leaf, i.e., youngest leaf with a ligule, was removed from each treatment. Leaves were placed against a black felt background under normal fluorescent lighting and photographed from a stationary camera pole set to a height of approximately fifty-eight (58) centimeters, and at an angle of approximately 40° offset from vertical. (FIG. 1A). An Olympus C-3030 (Olympus America Inc., Melville, N.Y.) digital camera was set to an ISO of 100, a shutter speed of 1/15 seconds, an aperature of 2.0, exposure compensation of 0, and to fluorescent light balance with the flash turned off. The threshold ranges in SigmaScan were set at 30 to 120 for hue, and 27 to 100 for saturation. Leaf images were taken with and without a green and yellow internal standard. The internal standard was nine (9) centimeter circular standardized color disks with RGB values of 0, 135 and 0 for the green standardized color disk and 225, 225 and 0 for the yellow standardized color disk. The digital images were collected in JPEG (Joint Photographic Experts Group) format with a color depth of 16.7 million colors, and an image size of 1280×960 pixels (260 kilobytes per image). After the leaves were photographed, average SPAD readings were taken from each leaf. The leaves were then dried at 85° C. until the weight was constant, at which point they were ground through a twenty (20) mesh screen and submitted for total nitrogen analysis via Micro-Dumas combustion by the Soil Test and Plant Analysis Laboratory at the University of Arkansas.

Greenhouse Study 2009:

A greenhouse study was conducted in 2009 to further compare digital image color values with SPAD and leaf nitrogen sufficiency or deficiency, as well as to evaluate the ability to calibrate cameras of varying quality using an internal standard within the digital images. Experimental design, treatment structure and sampling procedure were similar to the 2008 greenhouse study discussed infra except for number of cameras used, background color, threshold settings and calibration procedure.

Leaves were photographed against a pink felt background under normal fluorescent lighting. (FIG. 1B). Three (3) cameras were used to evaluate the internal standard for camera calibration, a Canon Power Shot S51S (Canon U.S.A., Inc., Lake Success, N.Y.), a Fugi Fine Pix A400 (Fuji Photo Film Co., Ltd, Minato-Ku, Tokyo, Japan), and a Canon Power Shot A20 (Canon U.S.A., Inc., Lake Success, N.Y.). Threshold ranges in SigmaScan were set at 7 to 126 for hue and 0 to 100 for saturation, which allowed for a complete analysis of the entire leaf without including any of the background in the final leaf color value. Differences among cameras DGCI values before and after calibration with the internal standard was evaluated by covariate analysis in which individual cameras served as the covariate.

The internal standard comprised a green and yellow nine (9) centimeter diameter circular standardized color disks, which were cut from X-Rite color paper (X-Rite Inc., Kentwood, Mich.). The standardized color disks were placed a minimum of about 1.5 inches away from the leaf so that the shadow between the leaf and standardized color disks did not cause the algorithm to see the objects as one, and therefore, would not exclude the value of the standardized color disks from the final leaf value. Also, placement of the standardized color disks was closest to the camera during photographing because the digital images were not taken from a direct vertical angle, and therefore, the further away the standardized color disks, the more they appeared oval instead of round. If oval, the algorithm would not recognize the standardized color disks as objects to be removed from the final leaf value. The green standardized color disk had a Munsell color value of 6.7GY 4.2/4.1, hue of 91, saturation of 38, brightness of 42, and DGCI of 0.5722, and the yellow standardized color disk had a Munsell color value of 5Y 8/11.1, hue of 66, saturation of 88, brightness of 100, and DGCI of 0.0733. After all the objects were scanned, the algorithm excluded values that were near circular (shape factor $\geq 0.8$), and averaged all other values, giving one final leaf DGCI value.

Greenhouse Results:

The 2008 and 2009 greenhouse studies demonstrate that the SPAD and DGCI values are in correlation with $r^2$ being greater than 0.91. Using the lighter background in the 2009 greenhouse study having a color in the visible spectrum away from the green spectrum allowed the threshold ranges to be expanded and the precision of the method and system of determining nitrogen levels from a digital image to be increased. The SPAD and DGCI values were closely associated with leaf nitrogen sufficiency or deficiency.

Figure 3A:
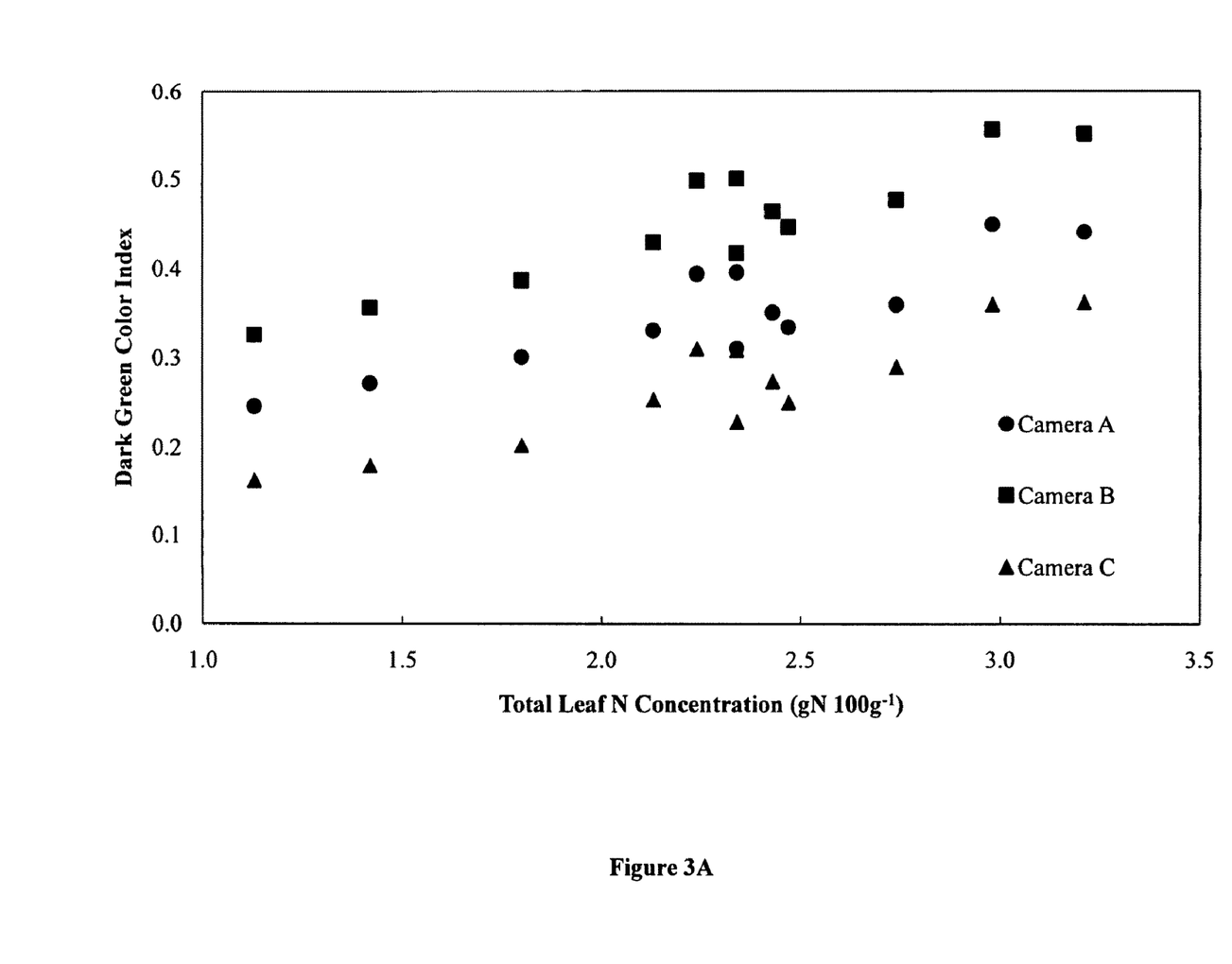
FIGS. 3A and 3B are graphical illustrations of dark green color index ("DGCI") values versus total leaf nitrogen concentration prior to (FIG. 3A) and after (FIG. 3B) using an internal standard to correct for differences among the three (3) cameras used to photograph the leaves in accordance with an illustrative embodiment of the system and method of determining nitrogen levels from a digital image disclosed herein.
Figure 3B:
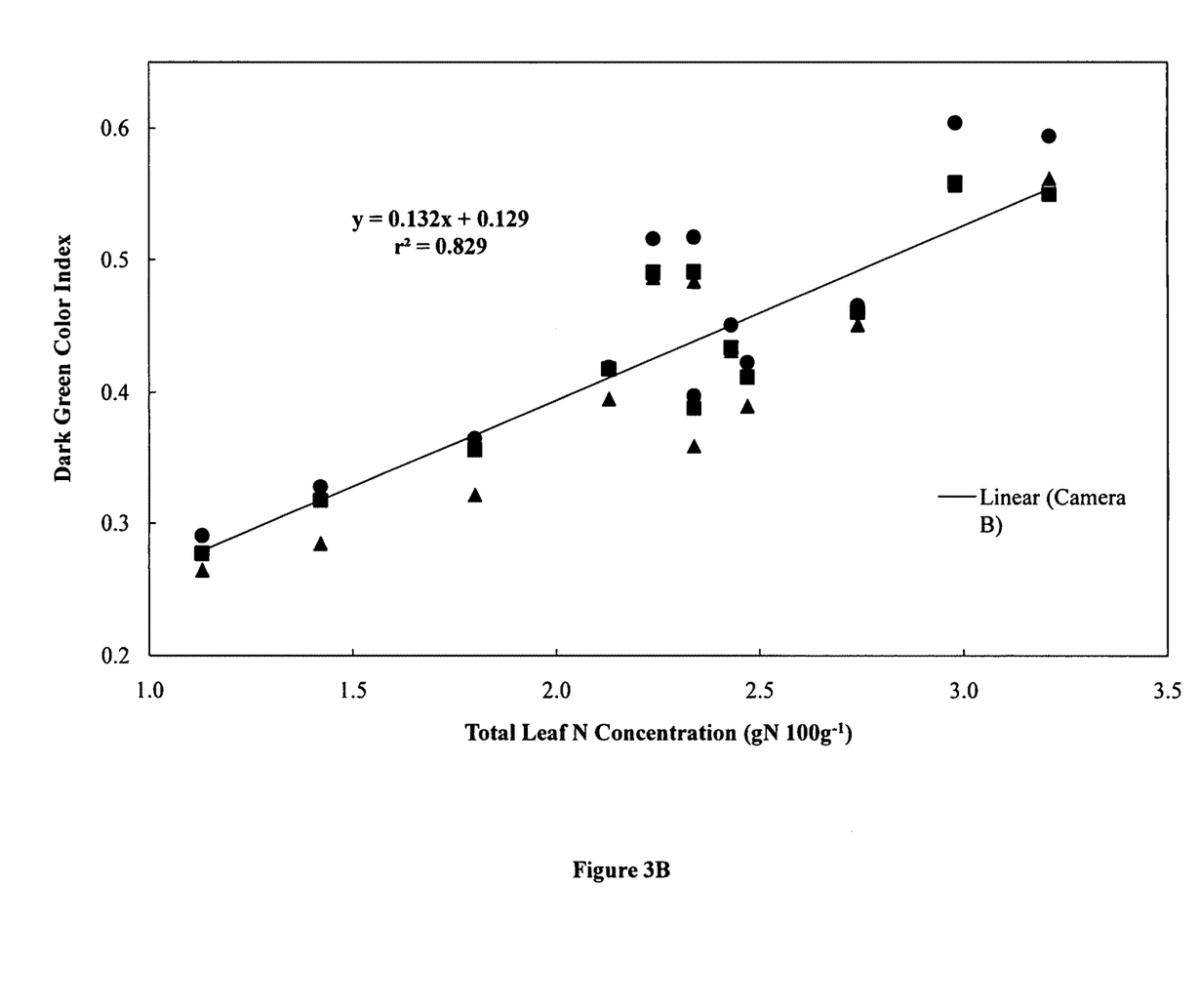
Figure 4A:
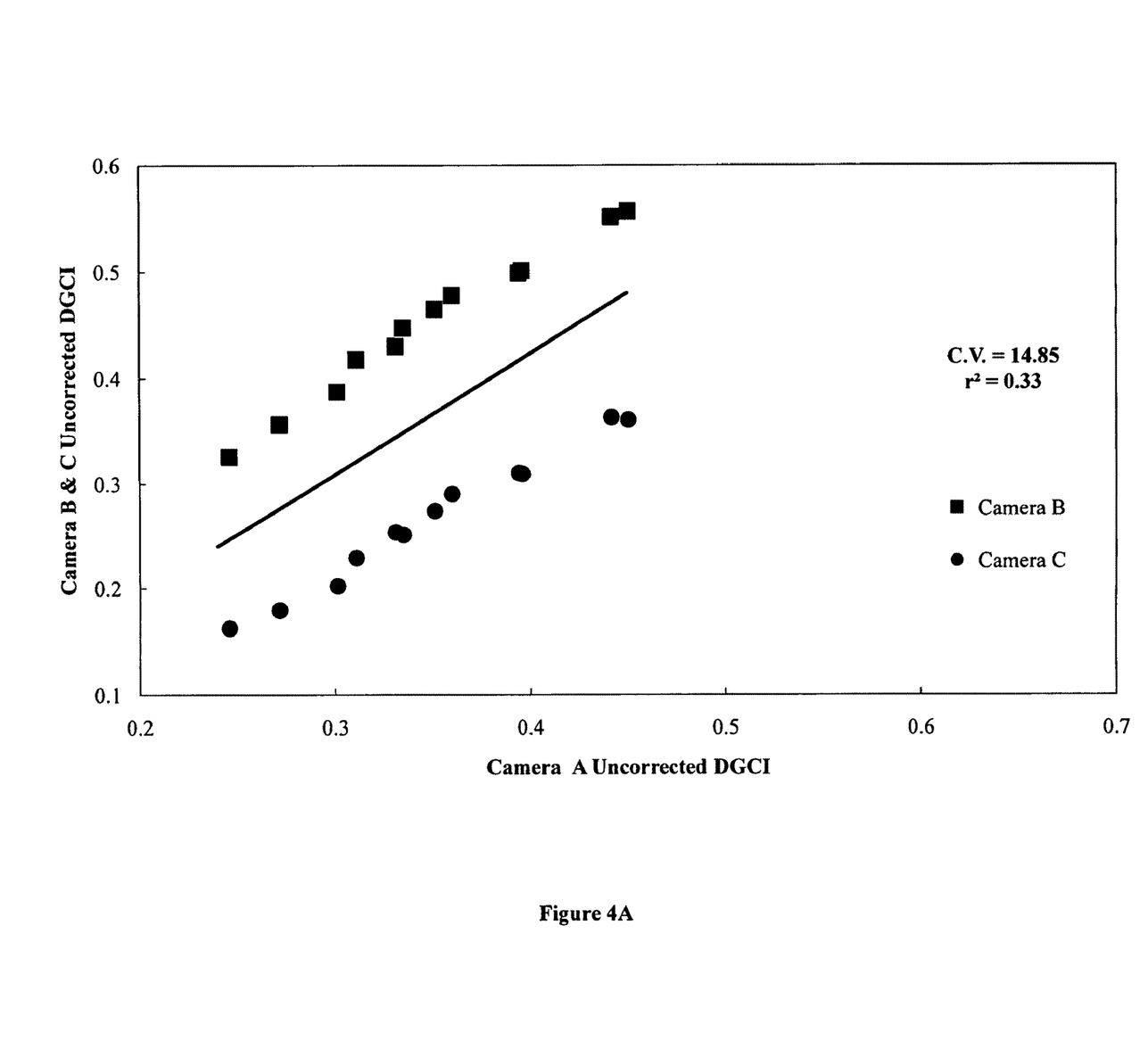
FIGS. 4A and 4B are graphical illustrations of DGCI values for cameras B and C versus the uncorrected DGCI value of camera A (FIG. 4A) and the corrected DGCI value of camera A (FIG. 4B) in accordance with an illustrative embodiment of the system and method of determining nitrogen levels from a digital image disclosed herein.
Figure 4B:
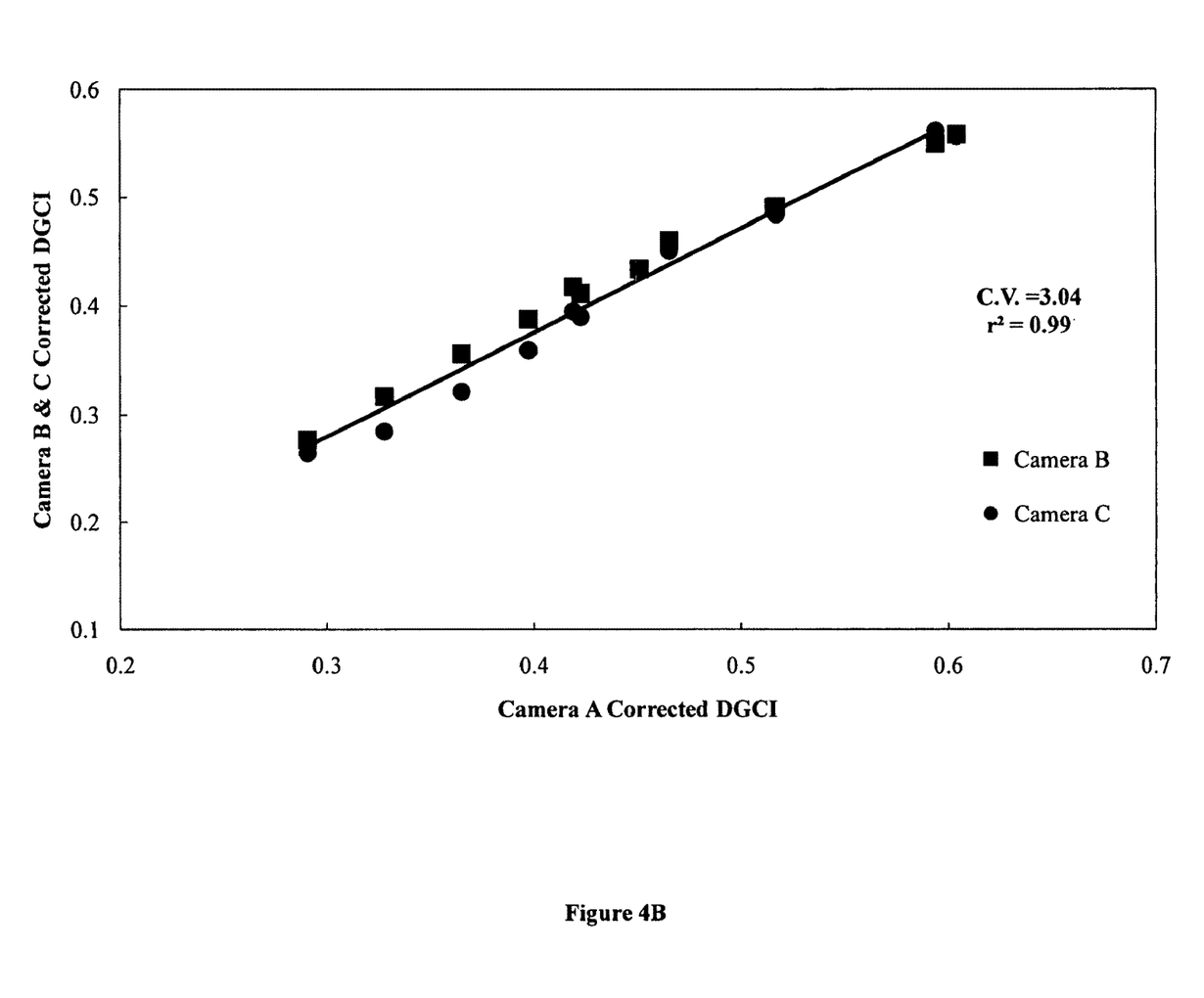

After calibration, the slope and intercepts for different cameras plotted against leaf nitrogen concentrations were not statistically different ($\alpha = 0.05$). FIGS. 3A and 3B are graphs illustrating the relationship of uncorrected DGCI values (FIG. 3A) and corrected DGCI values (FIG. 3B) versus leaf nitrogen concentration among the three (3) different cameras for plants sampled on Mar. 3, 2009. FIG. 4A shows the uncorrected DGCI values for cameras B and C plotted against the uncorrected value of camera A. As can be seen from FIG. 4B, calibration reduces the coefficient of variation from 14.85 to 3.04 and increases the adjusted $r^2$ from 0.33 to 0.99.

Field Study:

A field study was conducted in five (5) fields located in Fayetteville, Marianna, Keiser and Rohwer, Ark. The study design was a randomized complete block with three (3) to five (5) replications. Nitrogen treatments ranged from 0 to 336 kg/ha$^{-1}$ (hand applied urea). The sampling procedure was similar to the greenhouse studies discussed infra. Rows were spaced at approximately one-hundred (100) centimeters, and the plots were fertilized to meet soil test recommendations for nutrients, except nitrogen. The plots were kept well-watered using deionized water, and a crop yield was obtained.

Figure 5:
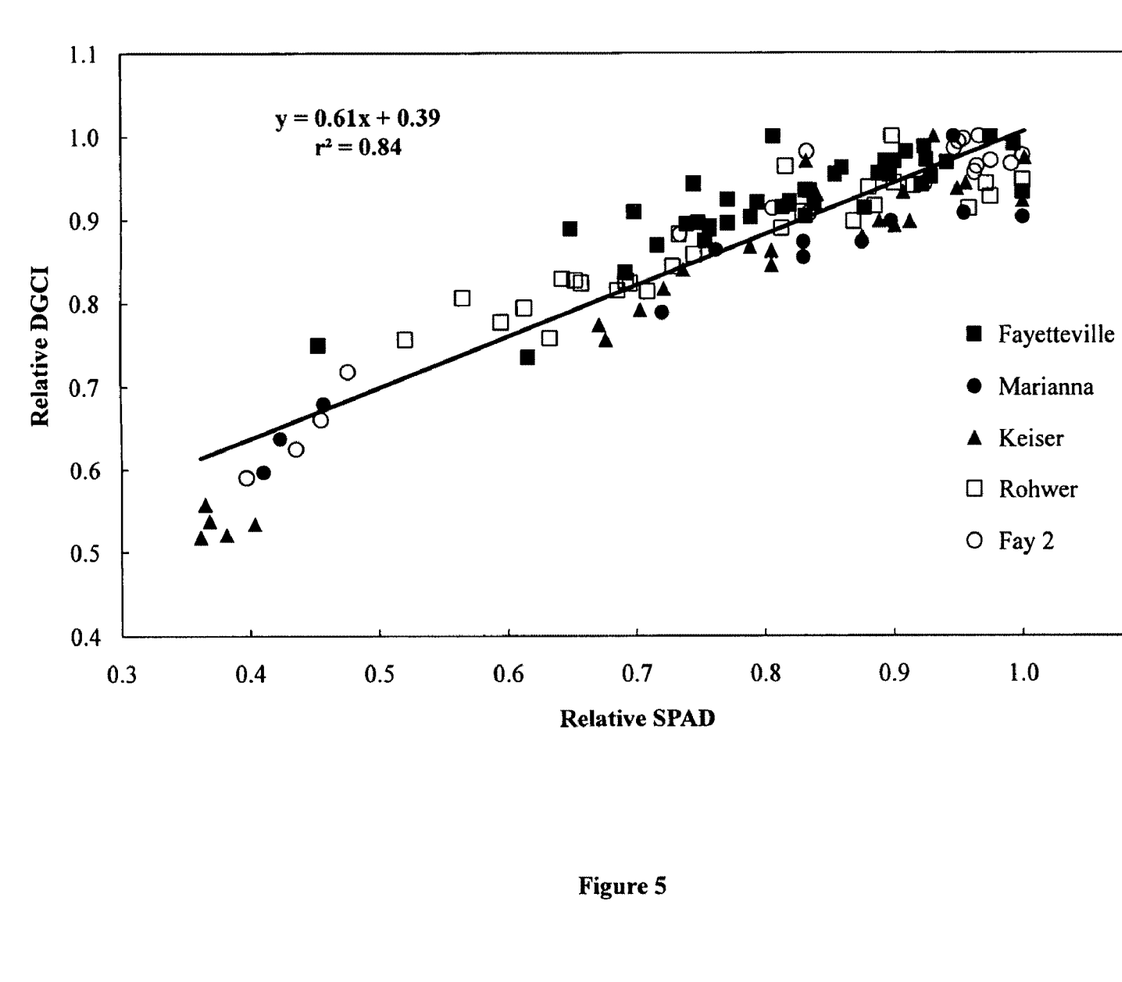
FIG. 5 is a graphical illustration of the relationship between relative DGCI values and relative SPAD values for all five (5) field locations in accordance with an illustrative embodiment of the system and method of determining nitrogen levels from a digital image disclosed herein.

Field Results—Relationship Among DGCI, SPAD, and Leaf Nitrogen Concentration:

DGCI and SPAD correlated for all field locations with coefficients of determination ranging from 0.72 to 0.95. The ability to use the internal standard as a means of calibrating the cameras greatly increased the agreement of SPAD and DGCI from 2008 to 2009. The relationship between relative DGCI and relative SPAD measurements for all locations is illustrated in FIG. 5, where the relative values of DGCI and SPAD can be used to show the correlation among treatments for multiple locations. Utilizing relative values lessens the effect of hybrid, soil type or environmental conditions. Composite regression data for all five (5) individual field locations and variables are listed in Table 1.

Field Results—Relationship of DGCI, SPAD, and Leaf Nitrogen Concentration to Yield:

DGCI and SPAD measurements taken at tasseling were closely associated with yield with coefficients of determination ranging from 0.67 to 0.88 for DGCI, and from 0.56 to 0.90 for SPAD. The two (2) lowest $r^2$ values for DGCI and SPAD were from the Fayetteville 1 location and occurred because the field was very sloped and nitrogen runoff was apparent. Plots were noticeably greener at the lower end of the field and resulted in abnormally high DGCI and SPAD values; furthermore, yield from plots with unknown amounts of available nitrogen could have caused coefficients of determination to be much lower than other the field locations. Average $r^2$ values of DGCI and SPAD plotted against yield for locations excluding Fayetteville 1 were 0.84 for DGCI and 0.86 for SPAD. The relative values of DGCI and SPAD plot-

TABLE 1

| Location | DGCI vs SPAD | DGCI vs leaf Nc | SPAD vs leaf Nc | Yield vs DGCI | Yield vs SPAD | Yield vs leaf Nc |
|---|---|---|---|---|---|---|
| Fayetteville 1 (Fay 1) | | | | | | |
| Slope | 0.004 | 0.083 | 14.08 | 46663 | 240.2 | 4795 |
| Intercept | 0.347 | 0.382 | 14.89 | −19825 | −4436 | −3999 |
| $r^2$ | 0.72 | 0.74 | 0.67 | 0.66 | 0.56 | 0.75 |
| n | 40 | 40 | 40 | 40 | 40 | 40 |
| Marianna | | | | | | |
| Slope | 0.006 | 0.134 | 20.91 | 42420 | 280.5 | 6138 |
| Intercept | 0.29 | 0.301 | 2.029 | −17127 | −5207 | −5221 |
| $r^2$ | 0.93 | 0.86 | 0.92 | 0.88 | 0.86 | 0.87 |
| n | 12 | 12 | 12 | 12 | 12 | 12 |
| Keiser | | | | | | |
| Slope | 0.008 | 0.165 | 18.79 | 28340 | 244.5 | 5339 |
| Intercept | 0.195 | 0.214 | 2.596 | −10858 | −5254 | −6485 |
| $r^2$ | 0.94 | 0.73 | 0.77 | 0.84 | 0.84 | 0.86 |
| n | 28 | 28 | 28 | 20 | 20 | 20 |
| Rohwer | | | | | | |
| Slope | 0.004 | 0.065 | 12.7 | 65302 | 344.8 | 4871 |
| Intercept | 0.341 | 0.423 | 19.65 | −29055 | −8440 | −2705 |
| $r^2$ | 0.82 | 0.85 | 0.87 | 0.81 | 0.83 | 0.90 |
| n | 28 | 28 | 28 | 28 | 28 | 28 |
| Fayetteville 2 (Fay 2) | | | | | | |
| Slope | 0.007 | 0.138 | 21.17 | 27217 | 206.6 | 4715 |
| Intercept | 0.247 | 0.28 | 1.07 | −9099 | −3038 | −3675 |
| $r^2$ | 0.95 | 0.80 | 0.92 | 0.83 | 0.90 | 0.87 |
| n | 18 | 18 | 18 | 18 | 18 | 18 |

Nc = Nitrogen concentration (g 100 g$^{-1}$) and Yield (kg ha$^{-1}$)

Figure 6:
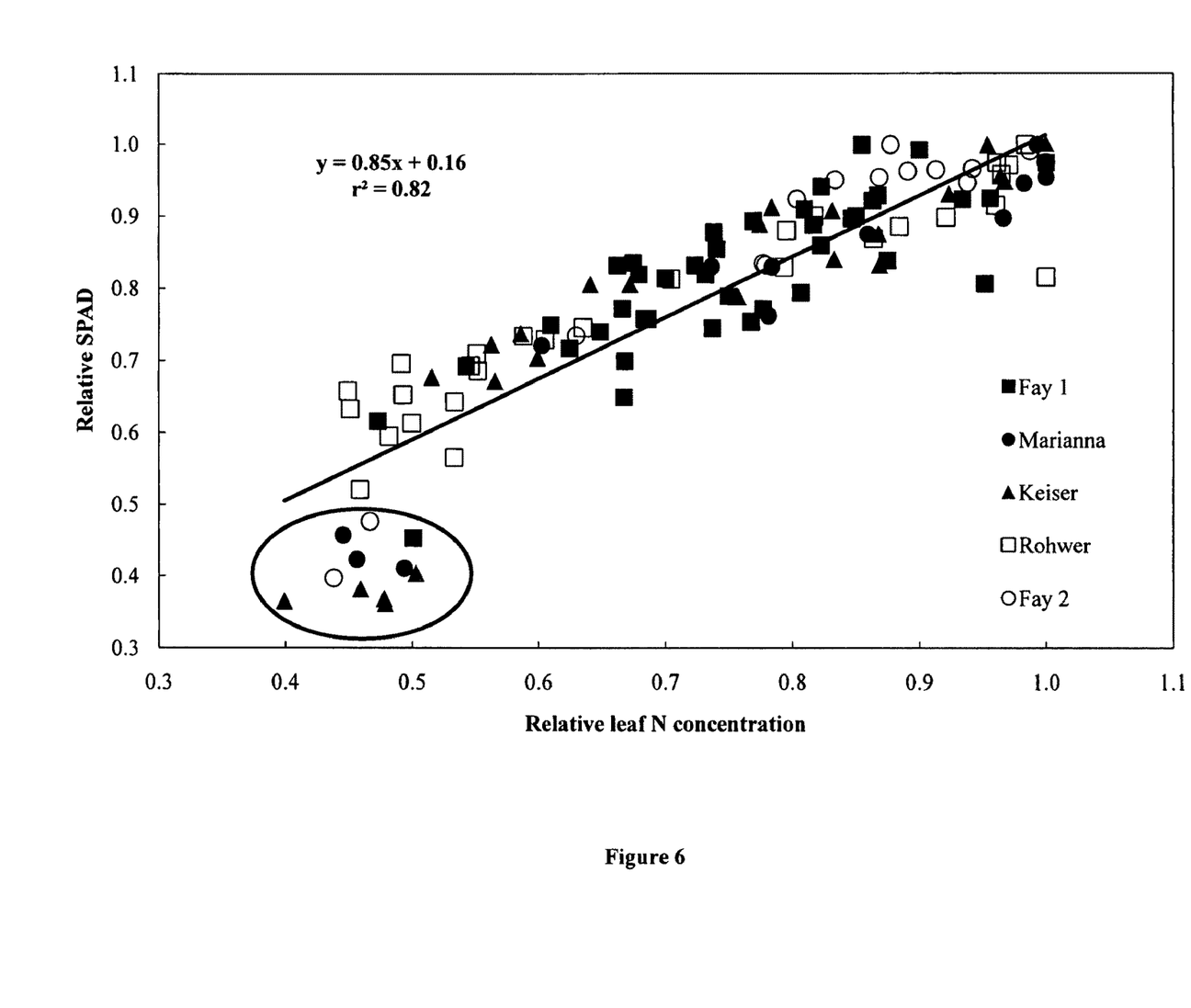
FIG. 6 is a graphical illustration of the response of the relative SPAD to an increase in the relative leaf nitrogen concentration in accordance with an illustrative embodiment of the system and method of determining nitrogen levels from a digital image disclosed herein.
Figure 7:
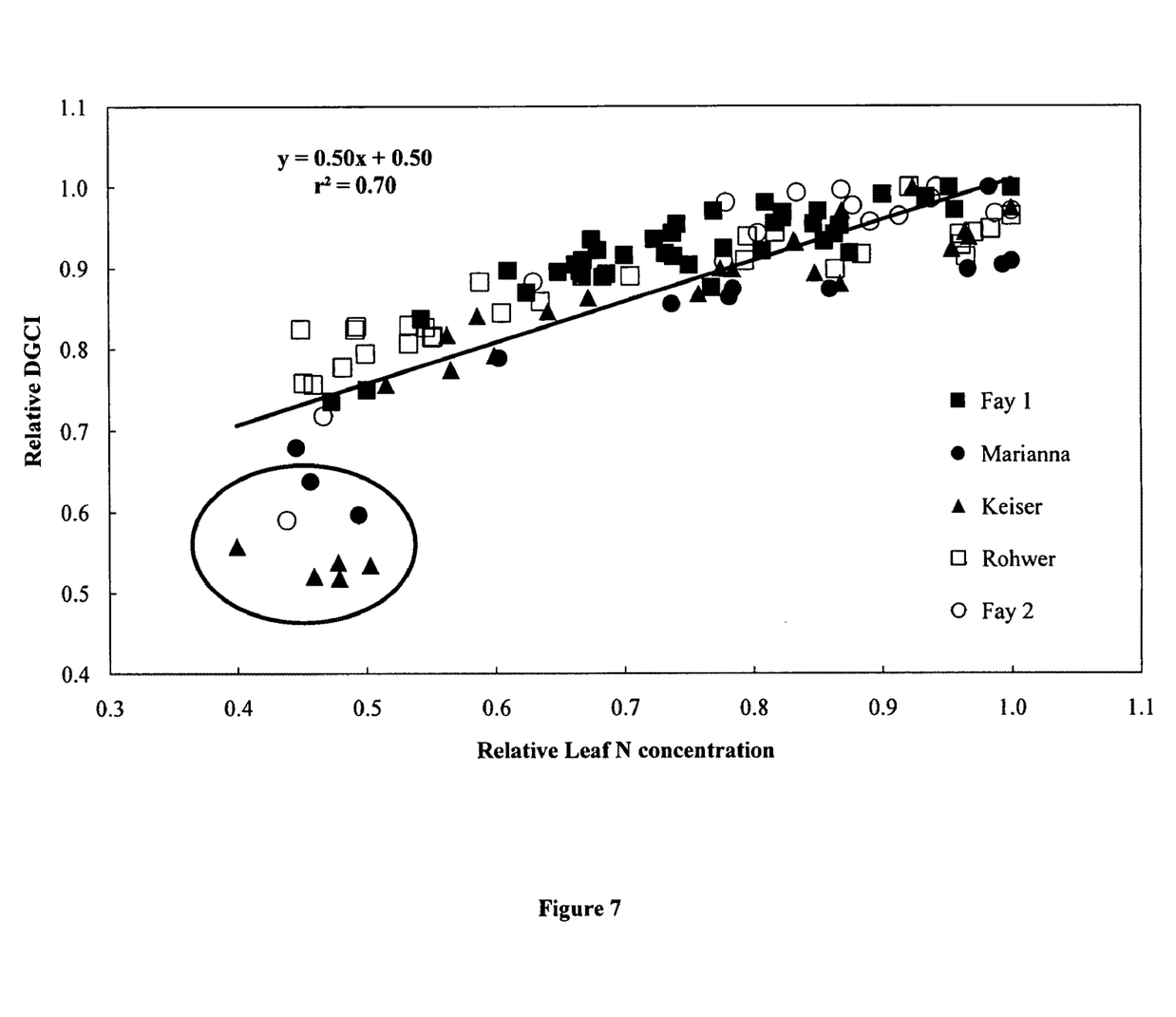
FIG. 7 is a graphical illustration of the response of the relative DGCI to an increase in the relative leaf nitrogen concentration in accordance with an illustrative embodiment of the system and method of determining nitrogen levels from a digital image disclosed herein.
Figure 8A:
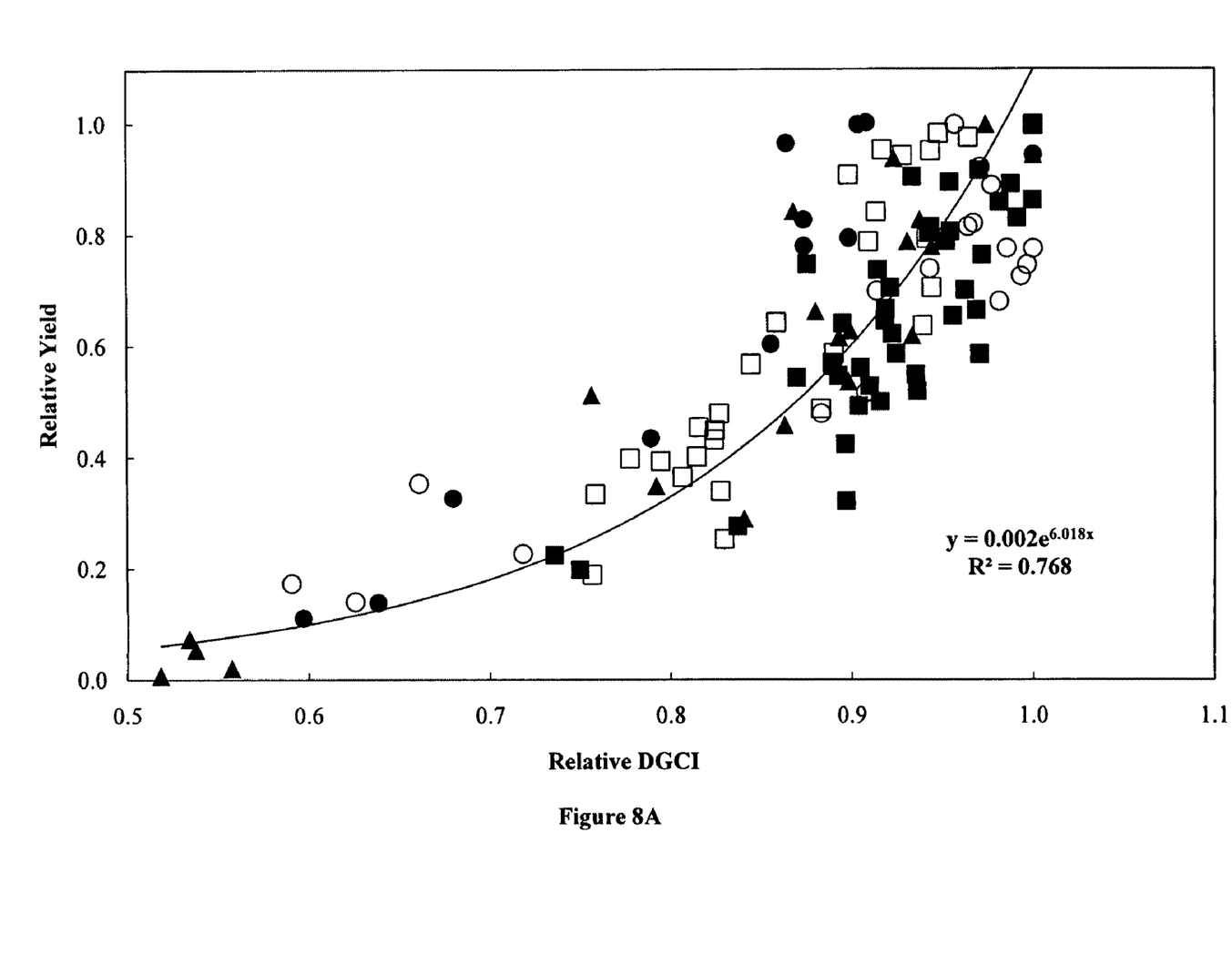
FIGS. 8A and 8B are graphical illustration of the response of relative yield of the crop to an increase in the relative DGCI value (FIG. 8A) and the relative SPAD value (FIG. 8B) sampled at tasseling for all five (5) field locations in accordance with an illustrative embodiment of the system and method of determining nitrogen levels from a digital image disclosed herein.
Figure 8B:
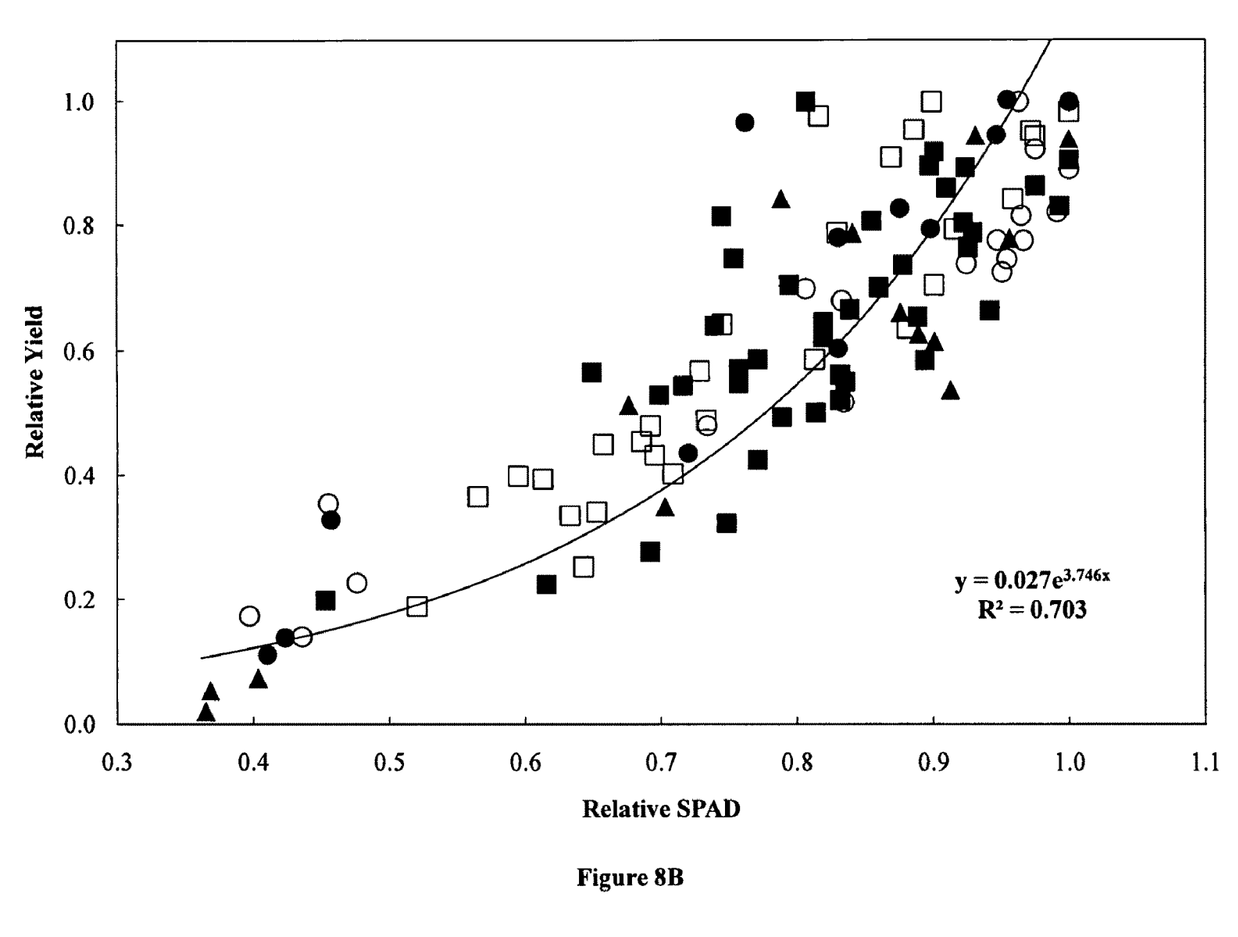

As can be seen, DGCI and SPAD values correlated with leaf nitrogen concentration for all field locations with average correlation coefficients of 0.80 for DGCI and 0.83 for SPAD. FIG. 6 graphically illustrates the response of relative SPAD to increasing relative leaf nitrogen concentration, while FIG. 7 graphically illustrates the relative DGCI response to increasing the relative leaf nitrogen concentration. As can be seen, the relative values of SPAD (FIG. 6) and DGCI (FIG. 7) to relative leaf nitrogen concentration were closely correlated even with five (5) different hybrids and multiple soil types for the five (5) different testing locations (FIG. 6). DGCI and SPAD both demonstrated accuracy in assessing leaf nitrogen concentration at tasseling. As illustrated in FIGS. 6 and 7, respectively, when relative leaf nitrogen concentration was less than 0.5 there was a poor association with either relative SPAD (FIG. 6) or relative DGCI (FIG. 7), and removing the circled values in FIGS. 6 and 7 increased the overall fit.

ted against relative yield for all field locations can be seen in FIGS. 8A and 8B, with FIG. 8A demonstrating the response of relative yield to increasing relative DGCI sampled at tasseling for all field locations and FIG. 8B illustrating the response of relative yield to increasing relative SPAD sampled at tasseling for all field locations.

The system and method of determining nitrogen levels from a digital image may utilize various delivery systems, such as a handheld electronic device capable of taking the digital image and running the appropriate analysis or fee-based, web-submission system. The handheld electronic device could take a digital photograph (with the internal standard) and could have the internal capacity to calculate the DGCI and provide an assessment to a user of the nitrogen status in real-time. Alternatively, the user could upload a digital image from a stand-alone computer, personal digital assistant, a camera or other electronic device through a suitable network connection, a local area network ("LAN") or other mechanism for connecting the electronic device to a remote computer having the appropriate software/application/algorithm loaded/packaged/embedded thereon. The user may pay a fee and have immediate diagnostic information relating to the nitrogen concentration and the yield of the crop based on the submitted digital image. The system and method of determining nitrogen levels from a digital image may be implemented through a computer program/application loaded on a standard computer device, such as a mainframe, desktop or other computer. For example, the computer device may have a central processor that controls the overall operation of the computer and a system bus that connects the central processor to one or more conventional components, such as a network card or modem. The computer device may also include a variety of interface units and drives for reading and writing data or files.

A library of digital images may be stored in a file repository and database of the remote computer of the system and method of determining nitrogen levels from a digital image. Each digital image can be referenced by a unique identifier. The system and method of determining nitrogen levels from a digital image may be implemented as a client/server application where the client electronic device having the digital image resident thereon connects to and communicates with the remote computer having the software and the algorithm loaded and resident thereon via the network connection. Upon submission, the client electronic device passes the digital image to the remote computer; the remote computer would perform the necessary steps to determine the nitrogen concentrations of the leaf and the yield from the submitted digital image. The remote computer transmits the nitrogen concentration and/or crop yield back to the client electronic device via the network connection. After transmitting the results from the remote computer to the client electronic device, the network connection may be disconnected. The client electronic device may then either display or print the results or allow the user to manipulate the results for the needs of the particular situation.

Whereas, the systems and methods have been described in relation to the drawings and claims, it should be understood that other and further modifications, apart from those shown or suggested herein, may be made within the spirit and scope of this invention.

What is claimed is:

1. A method for determining nitrogen levels of a nonlegume plant, said method comprising the steps of:
   a. acquiring an image with digital photography of a colored leaf from a crop of nonlegume plants with a background, said image further comprising an internal standard to account for differences in cameras or lighting conditions or both of said digital photography, and said background having a color in a portion of the visible spectrum away from the visible spectrum of the color of said leaf;
   b. performing an algorithm to determine a corrected dark green color index of said leaf in said image; and
   c. determining leaf nitrogen sufficiency or deficiency of said leaf in said image from said corrected dark green color index.

2. The method of claim 1 wherein said internal standard is a plurality of standardized color disks having a predetermined shape and a color representing a color value ranging from severely nitrogen deficient to nitrogen sufficient of said leaf.

3. The method of claim 2 wherein said standardized color disks further comprises a first standardized color disk having a yellow color representing a severely nitrogen deficient leaf and a second standardized disk having a dark green color representing a nitrogen sufficient leaf.

4. The method of claim 2 further comprising the step of placing said standardized color disks a distance away from said leaf during said digital photography to minimize any shadows between said leaf and said standardized color disks.

5. The method of claim 2 wherein said algorithm recognizes said shape of said standardized color disks and uses said standardized color disks as said internal standard to adjust for different cameras or lighting conditions or both.

6. The method of claim 1 wherein said color of said background is pink.

7. The method of claim 1 wherein said nonlegume plant is selected from the group consisting of corn, rice, wheat, cotton, potatoes or sugarcane.

8. The method of claim 1 further comprising the step of acquiring said image through a network connection.

9. The method of claim 2 wherein said algorithm comprising the steps of:
   a. calculating a dark green color index of said leaf in said image;
   b. calculating a dark green color index of said standardized color disks in said image; and
   c. calculating a corrected leaf dark green color index from said dark green color index of said leaf and said dark green color index of said standardized color disks.

10. The method of claim 9 wherein said step of calculating said dark green color index of said leaf in said image further comprises the steps of:
    a. obtaining absolute red, green and blue values of said leaf in said image;
    b. converting said absolute red, green and blue values to percentage red, green and blue values of said leaf in said image;
    c. converting said percentage red, green and blue values to absolute hue, saturation and brightness values of said leaf in said image;
    d. calculating average hue, saturation and brightness values from said absolute hue, saturation and brightness values of said leaf in said image; and
    e. converting said average hue, saturation and brightness values to said dark green color index of said leaf in said image.

11. The method of claim 10 wherein said dark green color index of said leaf in said image encompasses a dark green color on a scale of zero (0) to one (1) with values closer to one (1) representing a darker green.

12. The method of claim 9 wherein said step of calculating a dark green color index of said standardized color disks in said image further comprises the steps of:
    a. obtaining absolute red, green and blue values of said standardized color disks in said image;
    b. converting said absolute red, green and blue values to percentage red, green and blue values of said standardized color disks in said image;
    c. converting said percentage red, green and blue values to absolute hue, saturation and brightness values of said standardized color disks in said image;
    d. calculating average hue, saturation and brightness values from said absolute hue, saturation and brightness values of said standardized color disks in said image; and
    e. converting said average hue, saturation and brightness values to said dark green color index of said standardized color disks in said image.

13. The method of claim 12 wherein said dark green color index of said standardized color disks in said image encompasses a dark green color on a scale of zero (0) to one (1) with values closer to one (1) representing a darker green.

14. The method of claim 1 further comprising the step of estimating yield of said crop from said image as a function of said corrected dark green color index.

15. The method of claim 14 further comprising the step of transmitting said yield of said crop.

16. The method of claim 1 further comprising the step of estimating yield of said crop from said image based on said leaf nitrogen sufficiency or deficiency.

17. The method of claim 1 further comprising transmitting said leaf nitrogen sufficiency or deficiency.

18. A system comprising:
    at least one electronic device for taking an image of a colored leaf from a crop of said nonlegume plant;
    an image background having a color in a portion of the visible spectrum away from the visible spectrum of the color of said leaf;
    an internal standard to account for differences in cameras or lighting conditions or both of said image; and
    a central processing unit communicably attached to said electronic device via a network connection for performing an algorithm to determine a corrected dark green color index of said leaf in said image.

19. The system of claim 18 wherein said electronic device comprises a digital camera or a handheld electronic device having a camera and an algorithm to determine a corrected dark green color index of said leaf in said image.

20. The system of claim 18 wherein said internal standard are standardized color disks having a predetermined shape and a color representing a color value ranging from severely nitrogen deficient to nitrogen sufficient of said leaf.

21. The system of claim 20 wherein said standardized color disks further comprises a first standardized color disk having a yellow color representing a severely nitrogen deficient leaf and a second standardized disk having a dark green color representing a nitrogen sufficient leaf.

22. The system of claim 18 wherein said nonlegume plant is selected from the group consisting of corn, rice, wheat, cotton, potatoes or sugarcane.

23. A system for determining nitrogen levels of a nonlegume plant, said system comprising:
    an electronic device for taking an image of a colored leaf from a crop of said nonlegume plant;
    an external standard having a color in a portion of the visible spectrum away from the visible spectrum of the color of said leaf;
    an internal standard to account for differences in cameras or lighting conditions or both of said image, said internal standard representing a color value ranging from severely nitrogen deficient to nitrogen sufficient of said leaf; and
    a central processing unit communicably attached to said electronic device via a network connection for performing an algorithm to determine a corrected dark green color index of said leaf in said image.

24. The system of claim 23 wherein said electronic device comprises a digital camera or a handheld electronic device having a camera and an algorithm to determine a corrected dark green color index of said leaf in said image.

25. The system of claim 23 wherein said internal standard are standardized color disks having a predetermined shape.

26. The system of claim 25 wherein said standardized color disks further comprises a first standardized color disk having a yellow color representing a severely nitrogen deficient leaf and a second standardized disk having a dark green color representing a nitrogen sufficient leaf.

27. The system of claim 23 wherein said nonlegume plant is selected from the group consisting of corn, rice, wheat, cotton, potatoes or sugarcane.

* * * * *